(12) United States Patent
Lin et al.

(10) Patent No.: US 12,385,822 B1
(45) Date of Patent: Aug. 12, 2025

(54) CONCRETE TEST DEVICE AND METHOD BASED ON LOAD-CORROSION COUPLING ACTION

(71) Applicant: SUN YAT-SEN UNIVERSITY, Guangzhou (CN)

(72) Inventors: Peiyuan Lin, Zhuhai (CN); Xun Yuan, Zhuhai (CN); Yuepeng Liu, Zhuhai (CN); Baosong Ma, Zhuhai (CN); Sheng Huang, Zhuhai (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 0 days.

(21) Appl. No.: 19/192,678

(22) Filed: Apr. 29, 2025

Related U.S. Application Data (63) Continuation of application No. PCT/CN2024/116701, filed on Sep. 4, 2024.

(30) Foreign Application Priority Data

Dec. 8, 2023 (CN) .......................... 202311680560.1

(51) Int. Cl.
  *G01N 33/38* (2006.01)
  *G01N 3/16* (2006.01)
  *G01N 17/00* (2006.01)

(52) U.S. Cl.
  CPC ........... *G01N 17/002* (2013.01); *G01N 3/165* (2013.01); *G01N 33/383* (2013.01); *G01N 2203/0222* (2013.01); *G01N 2203/024* (2013.01)

(58) Field of Classification Search
  CPC ........................... G01N 33/383; G01N 17/002
  USPC ................................................ 422/53; 436/6
  See application file for complete search history.

(56) References Cited

FOREIGN PATENT DOCUMENTS

| CN | 101726439 A | 6/2010 |
|---|---|---|
| CN | 201819856 U | * 5/2011 |
| CN | 103439198 A | 12/2013 |
| CN | 103499483 A | 1/2014 |
| CN | 209432598 U | * 9/2019 |

\* cited by examiner

*Primary Examiner* — Arlen Soderquist
(74) *Attorney, Agent, or Firm* — Nitin Kaushik

(57) ABSTRACT

The present invention discloses a concrete test device and method based on a load-corrosion coupling action, relating to the technical field of corrosion experimental devices for concrete sewage pipelines. The device simulates a real environment of a sewage pipeline based on the load-corrosion coupling action, applies mechanical load and chemical corrosion effects to a concrete specimen simultaneously, and accelerates a corrosion effect on the concrete specimen by exposing the concrete specimen. According to the device, researches on mechanical properties of a concrete material under the load-corrosion coupling action are realized, and an assessment sample basis is provided for researches on aging characteristics of the concrete sewage pipelines. The present invention further discloses a concrete test method based on the aforementioned test device.

8 Claims, 6 Drawing Sheets

CONCRETE TEST DEVICE AND METHOD BASED ON LOAD-CORROSION COUPLING ACTION

CROSS-REFERENCE TO RELATED APPLICATIONS

The application claims priority to Chinese patent application No. 202311680560.1, filed on Dec. 8, 2023, the entire contents of which are incorporated herein by reference.

TECHNICAL FIELD

The present invention relates to the technical field of corrosion experimental devices for concrete sewage pipelines, and in particular, to a concrete test device and method based on a load-corrosion coupling action.

BACKGROUND

The construction of cities is inseparable from the laying of sewage pipelines. As a core structure of urban construction, the sewage pipelines are a decisive factor in determining whether a city can meet flood prevention standards. Currently, in urban environmental engineering, the sewage pipelines are mostly buried reinforced concrete structures. Due to their buried structural design, once issues arise in the sewage pipelines, the difficulty of detection and repair thereof is significantly high, resulting in high repair costs. Moreover, the construction engineering of the sewage pipelines is often the top priority of urban flood prevention projects, involving a wide range of aspects and substantial investments. Adopting a passive approach to address issues after they occur in the sewage pipelines is detrimental to the urban development and construction. Therefore, it is necessary to proactively prevent the potential structural issues in the sewage pipelines and study the aging characteristics of sewage pipelines. However, to study the aging characteristics of the sewage pipelines, it is inevitably linked to the durability of concrete used for preparing the sewage pipelines.

During operation, the sewage pipelines are subjected to various loads such as soil pressure from above and around the pipeline, traffic loads, water pressure, and self-gravity of the pipeline and sewage. Additionally, under the influence of a temperature field and the pipeline-soil interaction, the interior of the pipeline may experience different forms of mechanical actions such as tension, compression, bending, and shear. Furthermore, corrosive gases such as hydrogen sulfide are generated inside the sewage pipelines during operation. The combined action of loads and corrosion accelerates the aging process of the sewage pipelines, significantly impacting the durability of the concrete.

Currently, researches on concrete materials for the sewage pipelines primarily focus on the corrosion rules of the concrete under corrosive conditions and the mechanical properties of the concrete after corrosion. However, the aging of concrete for the sewage pipelines is often caused by the combined action of loads and corrosion, which frequently occur simultaneously. Researches that solely target the mechanical properties of concrete after corrosion result in a lack of reliable models and basis for assessing the aging characteristics of concrete for the sewage pipeline. This makes it difficult to achieve early prevention and resolution of structural damage issues in the sewage pipelines.

SUMMARY

The present invention aims to provide a concrete test device and method based on a load-corrosion coupling action, which can apply a load-corrosion coupling effect to concrete material, simulate a real environment of a sewage pipeline, obtain a concrete material close to the concrete sewage pipeline in service, and provide test specimens for researches on aging characteristics of concrete pipelines.

To achieve the above objective, the present invention adopts the following technical solutions:

A concrete test device based on a load-corrosion coupling action, specifically including a reactor box. And a reaction chamber and a load chamber that are airtightly isolated from each other are disposed in the reactor box;

a reaction assembly capable of generating corrosive gas is disposed in the reaction chamber, and the reaction assembly causes the corrosive gas to diffuse to fill an internal space of the reaction chamber; a plurality of load molds are disposed in the reaction chamber, and the load molds are used to carry concrete specimens and expose the concrete specimens to the corrosive gas; and a plurality of power assemblies capable of applying a mechanical load are disposed in the load chamber, and output ends of the power assemblies extend into the reaction chamber and are connected to corresponding load molds for applying a force towards a surface of the concrete specimens being corroded.

The concrete specimens can be prepared by different formulas according to concrete sewage pipeline material. The concrete specimens placed in the load mold are exposed in the reaction chamber, so that the corrosive gas generated by the reaction assembly can fully contact and react with all surfaces of the concrete specimens. The power assembly applies mechanical load such as tension, compression, bending, and shear to a corroded surface of concrete specimens based on different designs of load molds, so that the concrete specimens are affected by a load-corrosion coupling action, and concrete specimens close to the concrete sewage pipelines in service are obtained. By monitoring and statistically analyzing mechanical properties and corrosion conditions of the concrete specimens, an experimenter could establish a model for assessing and predicting acceleration effects of concrete aging for the sewage pipeline, so as to achieve prediction of an aging process of the sewage pipeline.

In an implementation, a heat source for generating a simulated temperature field for the concrete specimen is disposed in the reaction chamber, so as to provide a set temperature environment, such as a temperature environment close to a real sewage pipeline, for the concrete specimen placed in the load mold. The heat source is airtightly isolated inside the reaction chamber and is not in contact with the corrosive gas to prevent leakage of the corrosive gas. Specifically, the heat source includes a temperature control device disposed outside the reactor box, and the temperature control device is communicated to a heat duct extending into the reaction chamber; and a water bath heating assembly is disposed in the temperature control device, and water vapor generated by the water bath heating assembly is directed into the heat duct. Through heat exchange between the water vapor and the gas inside the reaction chamber, the temperature inside the reaction chamber is smoothly adjusted, thereby avoiding drastic temperature changes inside the reaction chamber.

In an implementation, the reaction assembly includes a reaction tank containing a reaction solution and a fan located above the reaction tank; and the reaction tank is communicated to a liquid duct, which is connected with a reservoir storing the reaction solution outside the reactor box. The reaction solution in the reservoir is supplied through a feeding device, flows into the reaction tank through the liquid duct, and reacts with the solution in the reaction tank to generate a corrosive gas such as a hydrogen sulfide gas. By controlling a feeding rate and a feeding amount of the reaction solution in the reservoir through the feeding device, a corrosive gas concentration inside the reaction chamber can be regulated and controlled.

In an implementation, the load mold includes an upper mold and a lower mold, where
the upper mold is connected to the output end of the power assembly and moves synchronously with the output end of the power assembly; and
the lower mold is fixed in the reaction chamber; a supporting plate for carrying the concrete specimen and a clamping part for clamping and fixing the concrete specimen are disposed in the lower mold; the supporting plate is kept in contact with the concrete specimen; and the clamping part is movable with respect to the concrete specimen and is in contact with a surface of the concrete specimen when the power assembly applies the mechanical load.

Before applying the mechanical load to the concrete specimen, all surfaces of the concrete specimen, except for a surface in contact with the supporting plate, can be exposed in the reaction chamber to be in full contact with the corrosive gas, so as to achieve corrosion conditions required for tests. Depending on the needs of different tests, the clamping part can also be attached to the surface of the concrete specimen before the power assembly applies the mechanical load. Thereby, the exposed surface of the concrete specimen in the reaction chamber can be controlled, and an area and a duration of the corrosive gas in contact with the concrete specimen can be further controlled, thus achieving the corrosive conditions required for the different tests.

In an implementation, each power assembly includes a screw rod which is driven to rotate by a power source and a transmission block which moves reciprocally in an axial direction along the screw rod; a synchronizing sleeve rotating synchronously with the transmission block is sleeved outside the transmission block, and the transmission block drives the synchronizing sleeve to rotate and move up and down; a plurality of rollable rolling members are disposed in the synchronizing sleeve; a load block for applying a load to the concrete specimen is sleeved outside the synchronizing sleeve, and the load block moves up and down with the synchronizing sleeve; and the rolling members are connected to the load block in a rollable manner. By adopting a combined structure of the screw rod and the transmission block, with the help of the power source such as a servo motor, a magnitude of the load applied to the surface of the concrete specimen can be accurately controlled, so that the load applied to the surface of the concrete specimen can be conveniently adjusted during a whole load-corrosion coupling test, and an ever-changing external force condition of the real sewage pipeline can be simulated. As a result, the concrete specimen obtained from the test device is closer to the concrete sewage pipeline in service, making the researches on the aging characteristics of concrete material more matched.

In an implementation, the test device is further provided with a monitoring module. The monitoring module monitors temperature, humidity, and corrosive gas concentrations inside and outside the reactor box. Based on data monitored by the monitoring module, the reaction assembly and the power assembly can automatically adjust and control their own working states and timely adjust corrosion reactions, mechanical loads, and other related factors, making the tests more accurate and effective.

Compared with the prior art, the concrete test device provided by the present invention has the following beneficial effects:

(1) the test device applies the load-corrosion coupling action to the concrete specimen, simulates the real environment of the sewage pipeline, and realizes researches on mechanical tests of the concrete material under dual actions of both load-corrosion, thereby providing an assessment sample basis for the researches on the aging characteristics of concrete;

(2) the test device allows the concrete specimen to be fully exposed in the corrosive gas, so that the specimen is in full contact with the corrosive gas, which accelerates a corrosion process of the specimen and effectively shortens the test time; and (3) the test device simultaneously applies mechanical load and chemical corrosion effects to the specimen, and utilizes the coupling action of load-corrosion to avoid the unicity in simulating concrete pipeline aging, making simulation of the tests more accurate and effective, and providing reliable sample basis for the researches on the aging characteristics of the concrete.

Based on the aforementioned test device, the present invention further provides a concrete test method based on a load-corrosion coupling action, specifically including the following steps:

(A) placing a concrete specimen into a load mold inside a reaction chamber, and exposing all surfaces of the concrete specimen, except for a surface in contact with the load mold, in the reaction chamber;

(B) sealing the reaction chamber, starting a reaction assembly, preparing a corrosive gas, and enabling the corrosive gas to diffuse to fill an internal space of the reaction chamber;

(C) after a corrosive gas concentration reaches a set value and a corrosion time reaches a set value, shutting down the reaction assembly, starting the power assembly, and applying a mechanical load to the concrete specimen, enabling the concrete specimen to be loaded with a load-corrosion coupling action; and (D) shutting down the power assembly after a loading time reaches a set value; and removing the corrosive gas and taking out the concrete specimen.

After the reaction assembly is shut down, the reaction chamber is filled with a sufficient concentration of corrosive gas, and the power assembly which is subsequently started is capable of subjecting the concrete specimen placed in the reaction chamber to the load-corrosion coupling action, and thus a sample affected by the load-corrosion coupling action is obtained.

When the power assembly is started, based on types of the mechanical load applied, the load mold will be attached to other surfaces of the concrete specimen based on support from the bottom. The force applied by the load mold to other surfaces of the concrete specimen will also affect the surface condition, which is also one of results observed in the tests.

In steps B, C, and D, the reaction assembly and the power assembly can be connected to a control module, and based on data fed back by a monitoring assembly in the reaction chamber, the control module outputs a control signal to control working states of the reaction assembly and the power assembly, thus achieving automated control of a test process.

According to the concrete test method based on a load-corrosion coupling action disclosed by the present invention, a concrete specimen close to concrete drainage pipeline material is used as a research object, a corrosion environment inside the drainage pipeline is simulated by feeding a corrosive gas, and basic loads such as tension, compression, bending, and shear are applied to the concrete specimen to simulate an actual stress on the drainage pipeline. After the tests are completed, the specimen in the device is taken out for flushing, photographing, scanning, and other operations to obtain data such as a corrosion depth and crack development of the concrete specimen; basic mechanical tests are performed on the specimen, mechanical properties are studied, and a model for assessing and predicting acceleration effects of aging is further established, providing a reliable sample basis for the researches on the aging characteristics of concrete pipelines.

In the figures: 1. reactor box; 2. reaction chamber; 3. load chamber; 4. supporting plate; 5. reservoir; 6. peristaltic pump; 7. heat duct; 8. reaction tank; 9. fan; 10. liquid duct; 11. upper tension mold; 11a. attachment portion; 11b. clamping portion; 12. lower tension mold; 13. upper pressure mold; 14. lower pressure mold; 15. upper bending force mold; 16. lower bending force mold; 17. upper shear force mold; 17a. moving member; 17b. compression-shear member; 18. lower shear force mold; 19. power assembly; 19a. servo motor; 19b. screw rod; 19c. transmission block; 19d. synchronizing sleeve; 19e. accommodating cavity; 19f. spring; 19g. connecting plate; 19h. ball; 19i. load block; 19j. annular groove; 20. internal monitoring module; 21. external monitoring module.

DETAILED DESCRIPTION OF THE EMBODIMENTS

The detailed implementation of the present invention is further described in detail below with reference to the accompanying drawings and embodiments. These embodiments are only intended to illustrate the present invention rather than to limit the scope thereof.

In the description of the present invention, it should be understood that, when an element is described to be "fixed to" or "disposed on" another element, it may be directly positioned on another element or indirectly positioned on another element. When an element is described to be "connected to" another element, it may be directly connected to another element or indirectly connected to another element. The terms "mounted", "attached", "connected" should be understood in a broad sense, e.g., it may be a fixed connection, a detachable connection or an integral connection; it may be a mechanical connection or an electrical connection; it may be a direct attachment, or an indirect attachment through an intermediate medium; and it may be a communication within two elements or an interaction relationship between two elements. For those of ordinary skill in the art, the specific meanings of the above terms in the present invention can be understood on a case-by-case basis.

In the description of the present invention, it should be understood that the orientations or positional relationships indicated by the terms "height", "upper", "lower", "vertical", "horizontal", "top", "bottom", "inner", "outer", etc. used herein are in accordance with those shown in the accompanying drawings of the present invention, and are intended only for the convenience of describing the present invention and simplifying the description, rather than for indicating or implying that the referred devices or elements must be provided with a particular orientation, and constructed and operated in the particular orientation, and thus, it cannot be understood as a limitation to the present invention.

In the description of the present invention, it should be understood that the terms "first" and "second" used herein are merely intended for description, and shall not be understood as an indication or implication of relative importance or an implicit indication of a quantity of indicated technical features. Therefore, a feature limited by "first" or "second" may explicitly or implicitly include one or more of such features.

Embodiment 1

Figure 1:
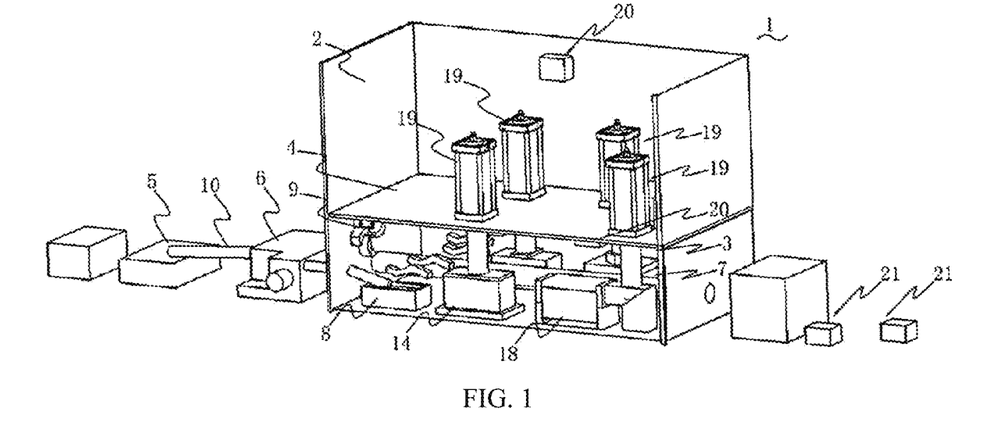
FIG. 1 is a schematic diagram of a test device according to Embodiment 1 of the present invention.

As shown in the figure, a concrete test device according to a preferred embodiment of the present invention uses a cubic concrete specimen as a test object and includes a reactor box 1, where the reactor box 1 is placed integrally in a fume hood to recycle and treat corrosive gases generated in a test process. A reaction chamber 2 and a load chamber 3 are disposed in the reactor box 1, and a supporting plate 4 is disposed between the reaction chamber 2 and the load chamber 3. The supporting plate 4 separates the reaction chamber 2 from the load chamber 3, allowing the reaction chamber 2 and the load chamber 3 to be airtightly isolated from each other. Side walls of the reactor box 1 are made of a transparent material, allowing an experimenter to observe interiors of the reaction chamber 2 and the load chamber 3.

A reservoir 5 for storing a sodium sulfide solution (reaction solution) and a peristaltic pump 6 communicated to the reservoir 5 are disposed outside the reactor box 1. The peristaltic pump 6 acts as a feeding device of the sodium sulfide solution, and supplies the sodium sulfide solution into the reaction chamber 2 to generate a hydrogen sulfide gas based on conditions set by the test. To ensure the safety of the test, the reservoir 5 and the peristaltic pump 6 are suitable to be placed together in the fume hood.

A temperature control device is integrated in the peristaltic pump 6, the temperature control device includes a water bath heating assembly, the water bath heating assembly is communicated to a heat duct 7 extending into the reaction chamber 2, and water vapor generated by the water bath heating assembly is directed into the heat duct 7. The heat duct 7 needs to be airtightly isolated inside the reaction chamber 2 to prevent leakage of the hydrogen sulfide gas inside the reaction chamber 2.

A reaction tank 8, a fan 9, a liquid duct 10, and a plurality of load molds are disposed in the reaction chamber 2, where the reaction tank 8 contains hydrochloric acid (reaction solution) for reacting with the sodium sulfide solution to generate a hydrogen sulfide gas;

the fan 9 is disposed above the reaction tank 8, and a direction of an airflow ejected by the fan 9 faces towards a location of the lower mold; and The liquid duct 10 is located above the reaction tank 8, extends outside the reactor box 1, and is communicated to the peristaltic pump 6; the sodium sulfide solution fed by the peristaltic pump 6 is conveyed to the reaction tank 8 through the liquid duct 10 and reacts with the hydrochloric acid; and the liquid duct 10 is connected to the reactor box 1 in a sealed manner.

Figure 2:
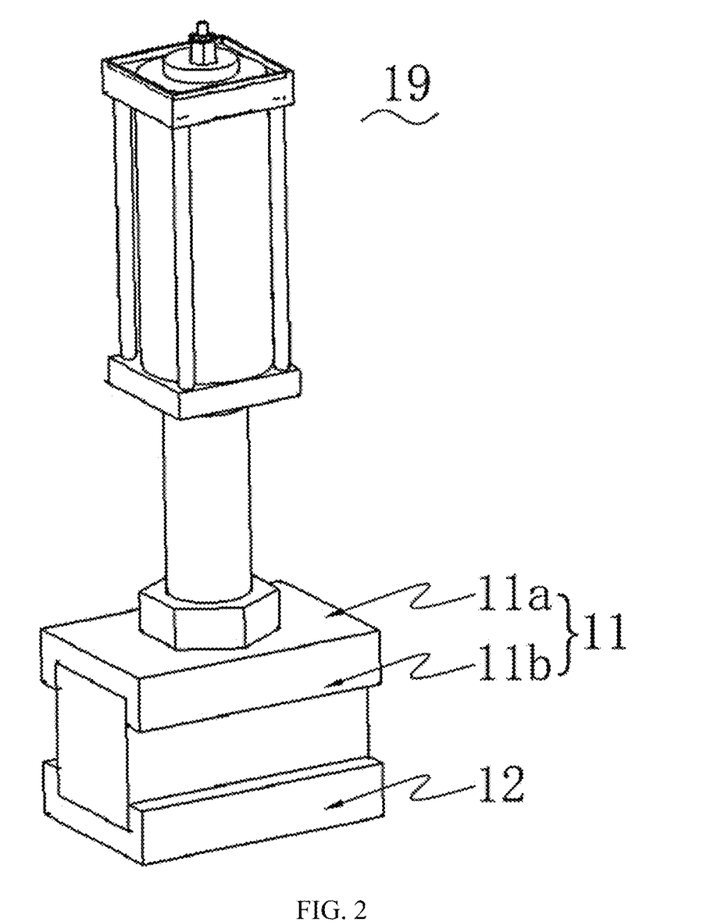
FIG. 2 is a schematic diagram of a first load mold according to Embodiment 1 of the present invention.

Based on types of mechanical load that needs to be applied, the load molds can be designed in a variety of styles, so that the experimenter can select the load molds with corresponding designs based on the style and shape of the concrete specimen. The plurality of load molds are suitably arranged in parallel, facilitating the hydrogen sulfide gas to be in contact with the concrete specimen in each load mold after diffusion. In Embodiment 1, the load molds adopt the following structural design:

(1) a first load mold: the first load mold is used to apply a tension load and includes an upper tension mold 11 and a lower tension mold 12. The upper tension mold 11 is fixed to an output end of the power assembly and moves with movement of the output end. The lower tension mold 12 is fixed in the reaction chamber 2 for supporting the concrete specimen. The upper tension mold 11 and the lower tension mold 12 are each provided with an attachment portion 11a parallel to the top/bottom of the concrete specimen and a clamping portion 11b capable of reciprocally approaching/moving away from the attachment portion 11a, where the attachment portion 11a is attached to the top/bottom of the concrete specimen based on its own location, respectively, and the corresponding clamping portion 11b is clamped on sides of the concrete specimen.

Figure 3:
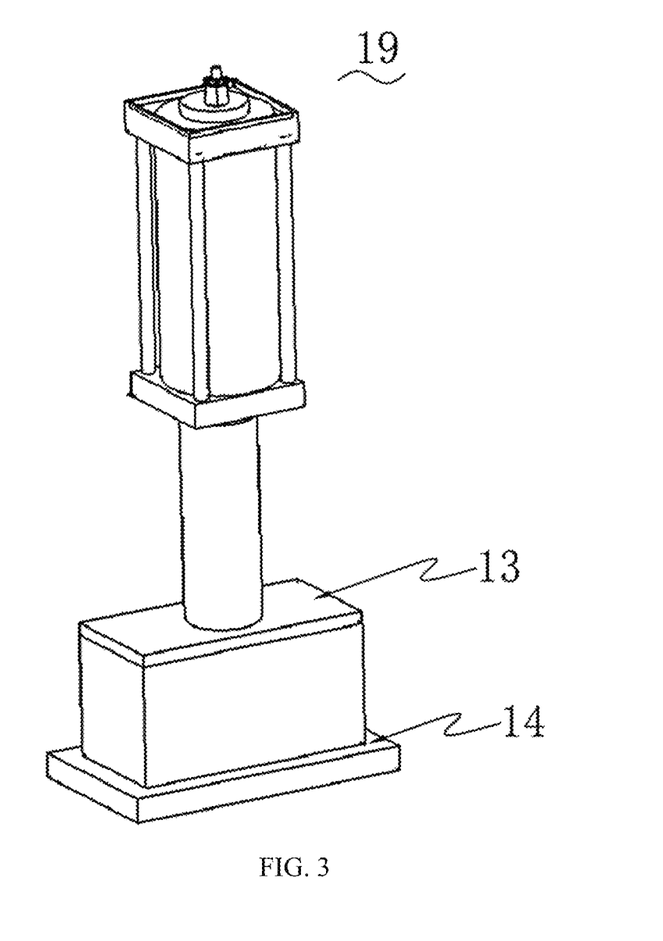
FIG. 3 is a schematic diagram of a second load mold according to Embodiment 1 of the present invention.

(2) a second load mold: the second load mold is used to apply a pressure load and includes an upper pressure mold 13 and a lower pressure mold 14. The upper pressure mold 13 is of a plate-like structure, is fixed to the output end of the power assembly, and is covered on the top of the concrete specimen with the movement of the output end. The lower pressure mold 14 is fixed in the reaction chamber 2 for supporting the concrete specimen, and the lower pressure mold 14 is provided with a positioning edge arranged along a circumference of the concrete specimen for fixing a location of the concrete specimen.

Figure 4:
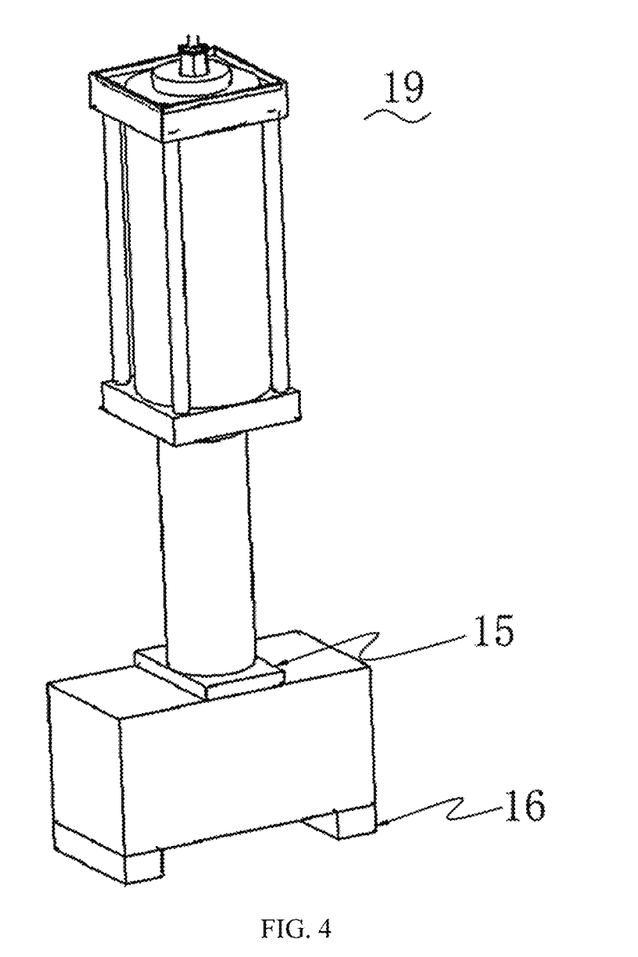
FIG. 4 is a schematic diagram of a third load mold according to Embodiment 1 of the present invention.

(3) a third load mold: the third load mold is used to apply a bending force load and includes an upper bending force mold 15 and a lower bending force mold 16. The upper bending force mold 15 is of a plate-like structure and has a cross-sectional area less than an area of the top of the concrete specimen; and the upper bending force mold 15 is fixed to the output end of the power assembly and is pressed against the top of the concrete specimen with the movement of the output end. The lower bending force mold 16 includes two supporting blocks that are symmetrically arranged, and the two supporting blocks are arranged at edges of the concrete specimen respectively to support the concrete specimen, allowing a middle portion of the concrete specimen to be suspended.

Figure 5:
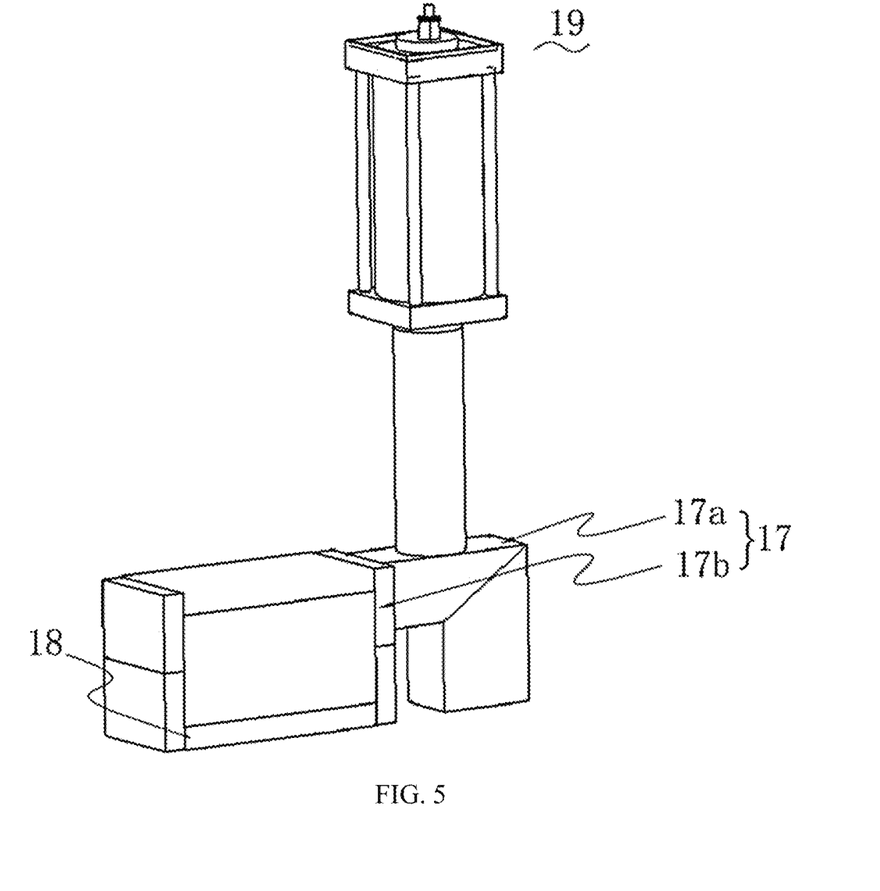
FIG. 5 is a schematic diagram of a fourth load mold according to Embodiment 1 of the present invention.

(4) a fourth load mold: the fourth load mold is used to apply a shear force load and includes an upper shear force mold 17 and a lower shear force mold 18. The upper shear force mold 17 includes a moving member 17a connected to the output end of the power assembly, the moving member 17a is connected to a compression-shear member 17b that is reciprocally movable with respect to the concrete specimen, and the compression-shear member 17b moves synchronously with the output end of the power assembly, is pressed against the surface of the concrete specimen, and applies a squeezing force in a height direction to the concrete specimen. The lower shear force mold 18 supports the concrete specimen, and allows the concrete specimen to be partially suspended and exposed to enter a region sheared by the compression-shear member 17b. When the compression-shear member 17b is pressed against an exposed region of the concrete specimen, the compression-shear member 17b and the lower shear force mold 18 cause the concrete specimen to generate a shear force in a direction of its own height.

Power assemblies 19 having a number corresponding to that of the load molds are disposed in the load chamber 3. Each power assembly 19 can use a conventional power output member such as a cylinder or an oil cylinder. The output end of the power assembly 19, such as a piston rod of the cylinder or the oil cylinder, extends into the reaction chamber 2 via the supporting plate 4 and is connected to the upper mold of the corresponding load mold.

The test device is further provided with a monitoring module. The monitoring module includes an internal monitoring module 20 and an external monitoring module 21, where the internal monitoring module 20 is placed inside the reactor box 1, is disposed inside the reaction chamber 2 and the load chamber 3, respectively, and is used to monitor temperature, humidity, and a corrosive gas concentration inside the reaction chamber 2 as well as a corrosive gas concentration inside the load chamber 3; and the external monitoring module 21 is placed outside the reactor box 1 and is used to monitor a corrosive gas concentration outside the reactor box 1.

The internal monitoring module 20 and the external monitoring module 21 are both connected to a control module outside the reactor box 1. The control module controls working states of components such as the peristaltic pump 6, the fan 9, the power assembly 19, and the water bath heating assembly based on monitoring data fed back by the internal monitoring module 20 and the external monitoring module 21, so that an environment inside the reaction chamber 2 and a stress state of the concrete specimen meet the requirements of test design.

Based on the aforementioned test device, taking an application of a tension load as an example, a test method using the test device of Embodiment 1 includes the following steps:

(A) starting a reaction chamber 2, and placing a concrete specimen into a lower tension mold, where during this process, an upper tension mold and a clamping portion 11b of the lower tension mold, except for an attachment portion 11a of the lower tension mold, are kept away from the concrete specimen, so that five surfaces of the concrete specimen are exposed in the reaction chamber 2;

(B) sealing a reactor, starting a control module, and outputting a control signal by the control module to start a peristaltic pump 6 and a water bath heating assembly, where the peristaltic pump 6 conveys a sodium sulfide solution to a reaction tank 8 through a liquid duct 10, so that the sodium sulfide solution reacts with hydrochloric acid to generate a hydrogen sulfide gas; and water vapor generated by heating of the water bath heating assembly enters a heat duct 7 and changes temperature inside the reaction chamber 2 by heat conduction, so as to construct a temperature field required for a test;

(C) outputting a control signal by the control module to start a fan 9, and blowing and diffusing the hydrogen sulfide gas generated by the reaction assembly, allowing the hydrogen sulfide gas to react with the concrete specimen placed in the lower tension mold; monitoring and feeding back the temperature, humidity, and a corrosive gas concentration in the reaction chamber 2 in real time by an internal monitoring module 20 placed in the reaction chamber 2; and controlling operation states of the peristaltic pump 6 and the water bath heating assembly based on data fed back by the internal monitoring module 20;

(D) after a concentration of the hydrogen sulfide gas reaches the set 40 ppm and a corrosion time in a set temperature environment reaches 30 days, outputting a control signal by the control module to shut down the peristaltic pump 6;

(E) outputting a control signal by the control module to start the power assembly 19, allowing an output end of the power assembly 19 to drive the upper tension mold to be pressed against the top of the concrete specimen, and allowing clamping portions 11b of both the upper tension mold and the lower tension mold to be pressed against surfaces of the concrete specimen such that the concrete specimen is clamped and fixed by the upper tension mold and the lower tension mold;

(F) controlling an action of the power assembly 19 based on a tension value set by the test, stretching the concrete specimen, performing a mechanical test on the concrete specimen corroded by the hydrogen sulfide gas, and enabling the concrete specimen to be in a state of load-corrosion dual action to obtain a tension strength $\tau_{L1}$ of the concrete specimen based on the load-corrosion dual action; and (G) shutting down the power assembly 19, removing the hydrogen sulfide gas in a box of the reaction chamber 2, and taking out the concrete specimen.

Mechanical property data and three-dimensional data of the above-mentioned concrete specimen loaded with a coupling action, an untested concrete specimen, and a concrete specimen only experiencing a corrosion action are summarized and compared, and data differences (such as mechanical data differences, three-dimensional height differences, and corrosion surface depth differences) between the concrete specimen loaded with the coupling action and the untested concrete specimen, and between the concrete specimen only experiencing the corrosion action and the untested concrete specimen are taken to obtain acceleration effects of aging of the concrete specimens caused by dual action. In addition, by taking specimen sizes, loading levels, hydrogen sulfide concentrations, and corrosion durations, etc. as input parameters based on a statistical method, a model for assessing and predicting the acceleration effect of aging can be effectively established, thus providing a theoretical basis for predicting the degree of aging of sewage pipelines and preventing damages to the sewage pipelines.

In summary, the embodiments of the present invention provide a concrete test device and method based on a load-corrosion coupling action. By applying the load-corrosion coupling action to the concrete specimen and simulating the real environment of the sewage pipeline in service, researches on mechanical tests of the concrete material under dual actions of both load-corrosion can be realized, thereby providing an assessment basis for the researches on the aging characteristics of concrete.

Embodiment 2

Figure 6:
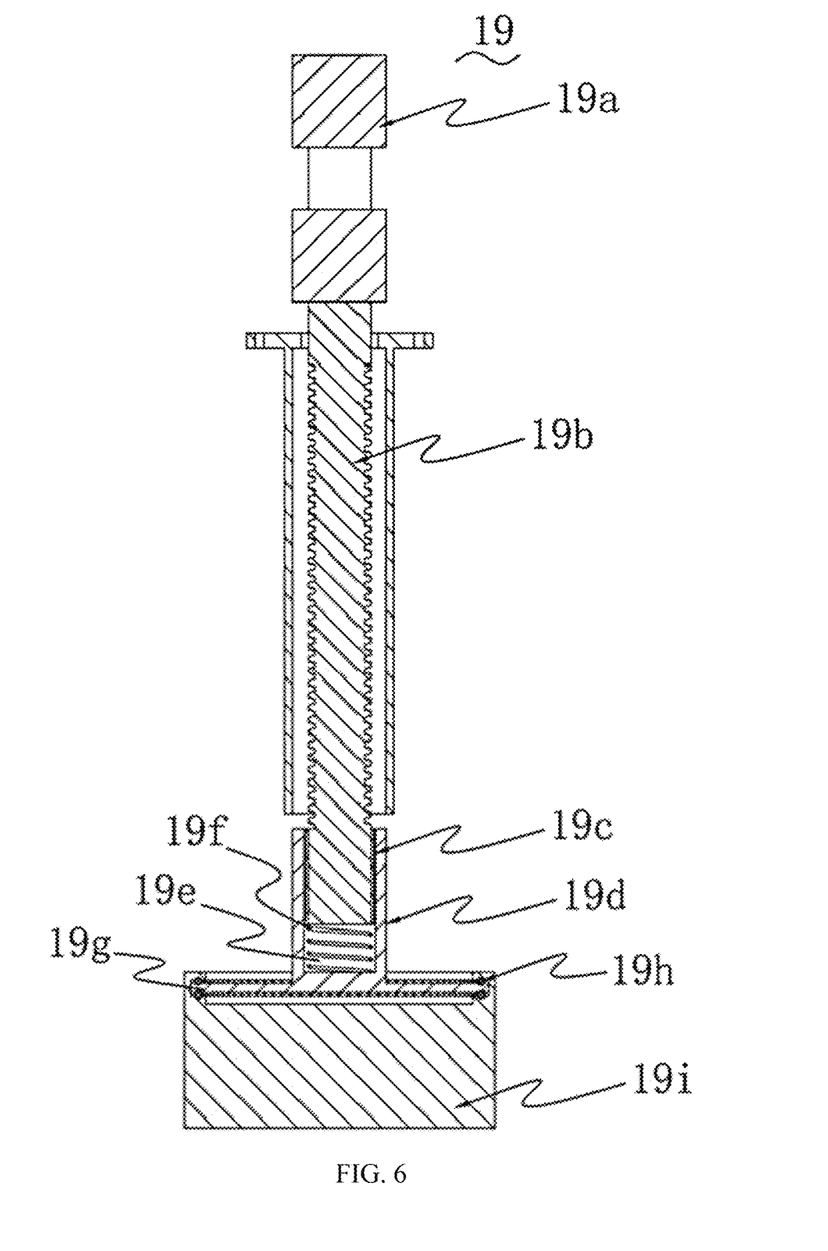
FIG. 6 is a schematic diagram of a power assembly according to Embodiment 2 of the present invention.

A concrete test device of Embodiment 2 differs from Embodiment 1 in that in Embodiment 2, the power assembly 19 adopts the following design:

As shown in FIG. 6, the power assembly 19 includes a screw rod 19b which is driven to self-rotate by a servo motor 19a as a power source and a transmission block 19c which moves reciprocally in an axial direction along the screw rod 19b, and a synchronizing sleeve 19d rotating synchronously with the transmission block 19c is sleeved outside the transmission block 19c.

An accommodating cavity 19e is disposed in the synchronizing sleeve 19d, and the screw rod 19b is penetrated into the accommodating cavity 19e. The transmission block 19c is arranged inside the accommodating cavity 19e and ascends and descends synchronously with the accommodating cavity 19e. A spring 19f is disposed between the bottom of the transmission block 19c and the bottom of the accommodating cavity 19e, for conducting and buffering an impact between the transmission block 19c and the synchronizing sleeve 19d.

The synchronizing sleeve 19d is provided with a connecting plate 19g in the shape of a column, and a plurality of balls 19h connected in the connecting plate 19g in a rollable manner are disposed at an end portion of the connecting plate 19g. Each ball 19h acts as a rolling member and protrudes from a surface of the connection plate 19g.

A load block 19i for applying a load to the concrete specimen is sleeved outside the synchronizing sleeve 19d. An annular groove 19j is disposed in the load block 19i, the connecting plate 19g is embedded in the annular groove 19j, and the balls 19h are connected to an interior of the annular groove 19j in a rollable manner, allowing the load block 19i to move up and down with the synchronizing sleeve 19d.

When the power assembly 19 receives a starting signal, the servo motor 19a drives the screw rod 19b to rotate, driving the transmission block 19c to drive the synchronizing sleeve 19d to descend in the axial direction along the screw rod 19b until the load block 19i is pressed against the surface of the concrete specimen. Due to a rolling connection between the synchronizing sleeve 19d and the load block 19i, the load block 19i does not need to rotate along with the synchronizing sleeve 19d during a descending process of the synchronizing sleeve 19d. Based on load conditions set by the test, the servo motor 19a controls the screw rod 19b to rotate, causing the transmission block 19c to continuously descend to squeeze the spring 19f, the spring 19f is driven to apply a force for squeezing towards the surface of the concrete specimen to the synchronizing sleeve 19d, and the force is conducted to the concrete specimen through the load block 19i, so as to apply a set load value to the concrete specimen.

By adopting a combined structure of the screw rod 19b and the transmission block 19c, a magnitude of the load applied to the surface of the concrete specimen can be accurately controlled, so that the load applied to the surface of the concrete specimen can be conveniently adjusted during a whole load-corrosion coupling test, and an ever-changing external force condition of the real sewage pipeline can be simulated. As a result, the concrete specimen obtained from the test device is closer to the concrete sewage pipeline in service, making the researches on the aging characteristics of concrete material more matched.

The above are only preferred embodiments of the present invention. It should be noted that, for those of ordinary skill in the art, a plurality of improvements and substitutions may be made without departing from the technical principle of the present invention, and the improvements and substitutions are also regarded to be within the protection scope of the present invention.

What is claimed is:

1. A concrete test device based on a load-corrosion coupling action, comprising a reactor box, wherein a reaction chamber and a load chamber that are airtightly isolated from each other are disposed in the reactor box;

a reaction assembly capable of generating a corrosive gas is disposed in the reaction chamber, and the reaction assembly causes the corrosive gas to diffuse to fill an internal space of the reaction chamber; a plurality of load molds are disposed in the reaction chamber, and the load molds are used to carry a concrete specimen and expose the concrete specimen to the corrosive gas; and a plurality of power assemblies capable of applying a mechanical load are disposed in the load chamber, and output ends of the power assemblies extend into the reaction chamber and are connected to corresponding load molds for applying a force towards a surface of the concrete specimen being corroded; each power assembly comprises a screw rod which is driven to rotate by a power source and a transmission block which moves reciprocally in an axial direction along the screw rod; a synchronizing sleeve is sleeved outside the transmission block, and the transmission block drives the synchronizing sleeve to rotate and move up and down; a plurality of rollable rolling members are disposed in the synchronizing sleeve; a load block for applying a load to the concrete specimen is sleeved outside the synchronizing sleeve, and the load block moves up and down with the synchronizing sleeve; and the rolling members are connected to the load block in a rollable manner.

2. The concrete test device according to claim 1, wherein a heat source for generating a simulated temperature field for the concrete specimen is disposed in the reaction chamber, so as to provide a set temperature environment for the concrete specimen placed in the load mold.

3. The concrete test device according to claim 2, wherein the heat source comprises a temperature control device disposed outside the reactor box, and the temperature control device is communicated to a heat duct extending into the reaction chamber; and a water bath heating assembly is disposed in the temperature control device, and water vapor generated by the water bath heating assembly is directed into the heat duct.

4. The concrete test device according to claim 1, wherein the reaction assembly comprises a reaction tank containing a reaction solution and a fan located above the reaction tank; and the reaction tank is communicated to a liquid duct extending outside the reactor box, and the liquid duct is communicated to a reservoir storing the reaction solution.

5. The concrete test device according to claim 1, wherein the load mold comprises an upper mold and a lower mold;

the upper mold is connected to the output end of the power assembly and moves synchronously with the output end of the power assembly; and the lower mold is fixed in the reaction chamber; a supporting plate for supporting the concrete specimen and a clamping part for clamping and fixing the concrete specimen are disposed in the lower mold; the supporting plate is kept in contact with the concrete specimen; and the clamping part is movable with respect to the concrete specimen and is in contact with a surface of the concrete specimen when the power assembly applies the mechanical load.

6. The concrete test device according to claim 1, comprising a monitoring module, wherein the monitoring module monitors temperature, humidity, and corrosive gas concentrations inside and outside the reactor box.

7. A concrete test method based on a load-corrosion coupling action, wherein the concrete test method applies the concrete test device according to claim 1 and comprises the following steps:

(A) placing a concrete specimen into a load mold of a reaction chamber, and exposing all surfaces of the concrete specimen, except for a surface in contact with the load mold, in the reaction chamber;

(B) sealing the reaction chamber, starting a reaction assembly, preparing a corrosive gas, and enabling the corrosive gas to diffuse to fill an internal space of the reaction chamber;

(C) after a corrosive gas concentration reaches a set value and a corrosion time reaches a set value, shutting down the reaction assembly, starting the power assembly, and applying a mechanical load to the concrete specimen, enabling the concrete specimen to be loaded with a load-corrosion coupling action; and (D) shutting down the power assembly after a loading time reaches a set value; and removing the corrosive gas and taking out the concrete specimen.

8. The concrete test method according to claim 7, wherein in steps B, C, and D, the reaction assembly and the power assembly are connected to a control module, and based on data fed back by a monitoring assembly in the reaction chamber, the control module outputs a control signal to control working states of the reaction assembly and the power assembly.

* * * * *